(12) United States Patent
Roberts et al.

(10) Patent No.: US 11,572,705 B2
(45) Date of Patent: Feb. 7, 2023

(54) SELF-CLEANING DOOR HANDLE COVER

(71) Applicant: PURE HOLD LIMITED, Catherington (GB)

(72) Inventors: Matthew Roberts, Havant (GB); David Burrell, Eastleigh (GB)

(73) Assignee: PURE HOLD LIMITED, Catherington (GB)

( * ) Notice: Subject to any disclaimer, the term of this patent is extended or adjusted under 35 U.S.C. 154(b) by 403 days.

(21) Appl. No.: 16/348,958

(22) PCT Filed: Nov. 10, 2017

(86) PCT No.: PCT/GB2017/053391
§ 371 (c)(1),
(2) Date: May 10, 2019

(87) PCT Pub. No.: WO2018/087559
PCT Pub. Date: May 17, 2018

(65) Prior Publication Data
US 2020/0190847 A1   Jun. 18, 2020

(30) Foreign Application Priority Data

Nov. 11, 2016   (GB) ..................................... 1619059
May 18, 2017   (GB) ..................................... 1708007

(51) Int. Cl.
*E05B 1/00*         (2006.01)
*A61L 2/238*        (2006.01)
(Continued)

(52) U.S. Cl.
CPC ............ *E05B 1/0069* (2013.01); *A61L 2/238* (2013.01); *A61L 2/28* (2013.01); *A61L 9/12* (2013.01);
(Continued)

(58) Field of Classification Search
CPC ....... E05B 1/0069; E05B 1/0061; A61L 2/238
See application file for complete search history.

(56) References Cited

U.S. PATENT DOCUMENTS 5,288,116 A      2/1994   Donofrio
2006/0230576 A1  10/2006  Meine
(Continued)

FOREIGN PATENT DOCUMENTS

DE   202005016217   12/2006
DE   102009053662   12/2010
(Continued)

OTHER PUBLICATIONS

PCT International Search Report dated Jan. 9, 2018, PCT Patent Application No. PCT/GB2017/053391.
(Continued)

*Primary Examiner* — Kevin Joyner
(74) *Attorney, Agent, or Firm* — Vierra Magen Marcus LLP

(57) ABSTRACT

Described herein is a cover for mounting to a door handle (30) comprises two parts (10, 12) configured for mutual locking engagement such that when the parts are brought into mutual locking engagement around a door handle (30) at least a portion of the door handle is substantially enclosed within a cavity (16) formed between the two parts (10, 12). At least a portion of at least one of the parts (10, 12) is coated, impregnated, or otherwise provided with a self-cleaning material. Also described is a push plate device comprising a first plate (72) for fixing to a door; and a second plate (71) configured to releasably attach to said first plate in order to form a composite plate structure (70). The second plate (71) is at least partly coated, impregnated, or otherwise provided with a self-cleaning material so that the composite plate structure (70) presents a self-cleaning external surface.

15 Claims, 9 Drawing Sheets

(51) Int. Cl.
  *A61L 2/28* (2006.01)
  *A61L 9/12* (2006.01)
  *E06B 7/28* (2006.01)
  *G04F 13/02* (2006.01)

(52) U.S. Cl.
  CPC .......... *E05B 1/0015* (2013.01); *E05B 1/0061* (2013.01); *E06B 7/285* (2013.01); *G04F 13/02* (2013.01); *A61L 2202/14* (2013.01)

(56) References Cited

U.S. PATENT DOCUMENTS

| 2011/0111000 | A1 | 5/2011 | Russell |
| 2011/0180621 | A1* | 7/2011 | Gruenbacher ............ A61L 9/12 239/34 |
| 2013/0206054 | A1 | 8/2013 | Vicente |
| 2014/0134095 | A1 | 5/2014 | Olson |

FOREIGN PATENT DOCUMENTS

| EP | 2754790 | 12/2013 |
| FR | 2892026 | 4/2007 |
| GB | 2402622 | 12/2004 |
| GB | 2436284 | 9/2007 |
| GB | 2500400 | 9/2013 |
| KR | 101132196 | 4/2012 |
| WO | 2013/167746 | 11/2013 |

OTHER PUBLICATIONS

PCT Written Opinion of the International Searching Authority dated Jan. 9, 2018, PCT Patent Application No. PCT/GB2017/053391.
GB Search Report dated Mar. 13, 2017, GB Patent Application No. GB1619059.7.
GB Search Report dated Dec. 6, 2017, GB Patent Applicatino No. GB1708007.8.
SteriTouch Ltd., "SteriTouch—All you need to know!," 2015 available at: www.steritouch.com.
Timestrip, Elapsed Time indicator, TS019 6 Months Data Sheet, 2017, available at: www.timestrip.com.
HoRe Logical Manufacturing UG, OClean Installation Quick Start Guide, Sep. 2016.
Communication Pursuant to Article 94(3) EPC dated Aug. 12, 2022, European Patent Application No. 17800585.6.

* cited by examiner

SELF-CLEANING DOOR HANDLE COVER

This application is a U.S. national stage filing of International Application No. PCT/GB2017/053391, filed Nov. 10, 2017, which claims priority to GB1619059.7 filed Nov. 11, 2016 and GB1708007.8 filed May 18, 2017, all of which are incorporated herein by reference in its entirety.

The present invention relates generally to door handles and devices for mounting to door handles, as well as push plates, and in particular to such devices having self-cleaning properties.

BACKGROUND

The problem of dirty door handles harbouring germs and spreading infections from one user to another is well known. Stainless steel is used widely on door handles due to its strength and durability but unfortunately stainless steel does not inhibit the growth of microorganisms that are deposited from users hands onto the surface, therefore facilitating the contamination of users hands as they pick up bacteria and viruses from the handle surface. This may be particularly problematic in hospitals, food processing facilities, or laboratories, where the consequences may be most severe, but may generally be a problem in various environments, including schools, hotels, and other public buildings. It is common to provide self-standing or wall mounted disinfectant sprays or pumps at a doorway to allow users to sanitise their hands. However, these rely on a user manually applying the disinfectant before entering the doorway and do nothing to address the problem of germs being incubated on the door handle.

Another approach may be to manufacture a door handle with self-cleaning properties. This approach requires specially installed door handles, and may be relatively expensive and inflexible.

A further approach may be to spray a chemical onto the surface of the door handle after each use so that any bacteria and viruses are killed. However, this approach would require the installation of a separate device for spraying the door handle, which device would need to be refilled regularly.

Another approach might be to adhesively stick a patch of self-cleaning material onto the door or door handle. However, it has been found that adhesive patches tend to rip, or peel off at the edges, especially when used for extended periods of time. It can also be difficult to accurately apply such adhesive patches and doing so will often result in bubbles appearing beneath the adhesive surface.

It is desired to provide an improved device for maintaining the cleanliness of a door handle.

SUMMARY

According to an aspect there is provided a device for mounting to a door handle, the device comprising:
a plurality of parts, the parts being configured for mutual locking engagement such that when the plurality of parts are brought into mutual locking engagement around a door handle at least a portion of the door handle is substantially enclosed within a cavity formed between the plurality of parts;
wherein at least a portion of at least one of the plurality of parts is coated, impregnated, or otherwise provided with a self-cleaning material.

When the plurality of parts are brought into mutual locking engagement, they together form a body defining a cavity. Thus, the plurality of parts forming the device may be fit around a door handle by bringing the respective parts into mutual locking engagement around the door handle such that at least a portion of the door handle is substantially enclosed between the parts. The device when installed thus effectively covers the door handle so that the user is forced to touch the device when opening the door. Any germs present on the user's hands are therefore transferred to a surface of the device, rather than the door handle itself. These germs may then be killed by virtue of the self-cleaning material provided on the device and the device may thus prevent germs from harbouring on the surface and thus prevent cross-contamination of germs from user to user.

It will be appreciated that because the device is mounted by fitting the parts together around the door handle, the device may be relatively easy to install, e.g. by a layperson, and, in embodiments, without requiring any tools. It will also be appreciated that the devices may be easily retrofit onto existing door handles without requiring the existing door handle to be replaced or removed. Furthermore, because a portion of the door handle is enclosed between the parts of the device in this way, the mounting of the device around the door handle may be relatively secure and robust, such that once the device is mounted it may be suitable for use for an extended period of time (e.g. months). When the device is mounted to a door handle in this way, the device essentially acts as a cover for the door handle. The device may therefore be referred to as a door handle cover or cover device.

In general, the device may comprise any number of parts, with the parts being connectable together to form a body of the device. That is, each part may be arranged for engagement with at least one of the other plurality of parts in order to connect the plurality of parts together.

In a preferred embodiment, the device is formed by fitting two parts together. Thus, the device may comprise a first part and a second part, wherein the first and second parts are configured for mutual locking engagement such that when the first and second parts are brought into mutual locking engagement said cavity is formed between the first and second parts. Accordingly, any reference herein to the parts, or plurality of parts, may in these embodiments be taken as a reference to the first and second parts.

In embodiments, the body of the device may comprise only the first and second parts, or consist essentially of the first and second parts. That is, the body of the device may be formed solely by fitting the two parts together.

The plurality of parts may generally have any suitable shape that permits their mutual locking engagement around a door handle. For instance, each of the plurality of parts may have an interior surface that substantially matches a contour of a (the) door handle. Thus, where the door handle is substantially cylindrical, e.g. a pull bar of the type shown in FIG. 1, each of the plurality of parts may have a curved interior surface such that when the plurality of parts are mutually engaged, a substantially cylindrical cavity is defined therebetween. Similarly, where the door handle is e.g. a lever style door handle, each of the plurality of parts may have a curved interior surface such that a cavity that substantially matches the shape of the door handle is defined therebetween.

Although the external form of the device may generally be less constrained than the interior, at least for ergonomic reasons, the exterior surfaces of the parts may also substantially match the shape of the door handle. The exterior surfaces of the parts may thus also be curved, e.g., and preferably, so as to form a substantially cylindrical outer surface and/or an hourglass shaped outer surface, when mutually engaged. The parts may be elongate. For example, the parts may each comprise a part (a radial arc) of a (hollow) cylinder. For instance, where two parts are provided, the parts may be provided substantially in the form of two (hollow) half cylinders, or semi cylinders.

In embodiments, the external surfaces of the parts, or at least the portions of the exterior surface that are touched by a user in typical intended use ("contact surfaces"), are substantially flat and/or smooth. For instance, these contact surfaces are preferably substantially free of perforations that could otherwise become clogged up with dirt or oil from the user's hands, thus creating a breeding ground for germs.

In embodiments, the parts are formed from a rigid or hard material e.g. a material that does not deform in use when contacted by a user (such as a foam or sponge). For example, the parts may suitably be formed from hard plastics material such as ABS plastics. The rigid or hard material may then suitably be coated with self-cleaning material (although the self-cleaning material may be provided to the rigid or hard material in other suitable ways, as desired).

The plurality of parts may each have a substantially similar shape. However, this need not be the case. For instance, one or more of the plurality of parts may comprise an elongate or other shape that generally defines the shape of the device whereas other parts of the plurality of parts may e.g. comprise connecting parts that facilitate the locking engagement of the plurality of parts, or other parts parts for carrying components to be mounted to or in the device.

At least some of the plurality of parts are provided with a self-cleaning material so that the device is "self-cleaning". It will be appreciated therefore that by at least a portion of at least one of the parts being coated, impregnated, or otherwise provided with a self-cleaning material, it is meant that at least a portion of the at least one of the parts that is touched by a user during typical intended use (a "contact surface") is provided with the self-cleaning material. In embodiments, substantially the whole of the device, or at least the exterior (outer (contact) surface (gripping surface)) of the device, may be coated, impregnated, or otherwise provided with self-cleaning material. In other less preferred embodiments, only a certain portion of the device is provided with the self-cleaning material.

It will be understood that a "door handle" is generally any attached object that allows a door to be opened. For example, in some embodiments, the devices described herein may be configured for mounting to a pull door handle comprising an extended substantially cylindrical bar mounted at either end to a door (e.g. as shown in FIG. 1). Thus, the cavity defined between the plurality of parts may extend throughout the body of the device such that the (i.e. or at least a portion of the) substantially cylindrical bar may be enclosed or received within the cavity. It will be appreciated however that by varying the shape of the cavity it is possible to mount the device to other shapes of door handles. For instance, as another example, the device may be designed to be mounted to a lever style door handle, in which case the cavity defined between the plurality of parts may be configured for mounting around the lever portion of the door handle.

The plurality of parts (or e.g. the first and second parts) may be configured for releasable mutual engagement. That is, the plurality of parts may be readily disengaged by a user, e.g. when it is desired to remove or replace the device. The device may thus be removed or replaced e.g. when the self-cleaning material wears out, and the device needs renewing, or when the device is broken and needs replacing. The plurality of parts may be capable of being repeatedly engaged and disengaged, such that a device may be removed and (re-)installed multiple times. For example, a device may be removed, re-coated with self-cleaning material, and then re-installed.

The plurality of parts (or e.g. the first and second parts) may be configured for mutual locking engagement via a press fit.

The plurality of parts (or e.g. the first and second parts) may be engaged and/or disengaged without using any tools, i.e. by virtue of the press fit alone.

The plurality of parts (or e.g. the first and second parts) may thus be provided with one or more tabs, or clips, for engaging with corresponding portions, or recesses, on the other parts (or other part) in order to allow the parts to be mutually engaged. For example, where the device is formed of two parts, the first part may have a first tab that fits into a first recess of the second part, wherein the first tab and first recess define a pivot point, such that when the first tab is inserted into the first recess, the first part may be pivoted towards the second part. The first part may further include a second tab that clips into a second recess of the second part in order to releasably lock the first and second parts together.

The device may have an effective shelf life before the self-cleaning material wears out and the device may need to be replaced or renewed. For example, where the self-cleaning material is provided as a coating, the coating will wear over time, and e.g. become scratched, with such scratches potentially harbouring germs. As the coating material is consumed, it will eventually therefore need to be replaced.

Thus, the device may comprise an indicator for providing a visual indication of a condition of the device such as a condition that the device should be replaced or renewed and/or a visual indication of an elapsed time period.

The indicator may indicate an elapsed time after activation of the indicator.

The indicator may be activated when the plurality of parts, or at least some of the plurality of parts, (or e.g. the first and second parts) are brought into mutual locking engagement around a door handle. That is, the act of bringing the plurality of parts into mutual locking engagement around the door handle may serve to activate the indicator in order to minimise user interaction and so that the indicator provides a reliable and precise indication of how long the device has been used for.

The indicator may be mounted within the cavity. For example, the indicator may be mounted on the interior of one of the plurality of parts forming the device, e.g. on the first and/or second part such that when the part carrying the indicator is pressed against a door handle, the force exerted by the door handle on the part activates the indicator. The indicator may be activated by depressing a button, or breaking a seal.

The indicator may comprise a colourant, wherein the colourant is released upon activation of the indicator and caused to wick a substrate, wherein the amount of wicking indicates an elapsed time period.

The device may further comprise one or more pieces of gripping material for preventing or reducing relative movement between the device and a door handle received within the cavity. That is, the one or more pieces of gripping material may, in use, act to prevent or reduce relative movement between the body of the device and a door handle to which the device is mounted. The gripping material may comprise an insert e.g. that may be provided on one or more of the plurality of parts (or e.g. the first and second parts) forming the device. The pieces of gripping material may thus be suitably shaped for insertion into the one or more of the plurality of parts of the device. The gripping material may extend along substantially the whole length of the device, or may extend along only a portion or portions of the length of the device.

The gripping material may allow the device to retrofit to a range of different size (e.g. diameter) door handles. The gripping material may be compressed between the body and the door handle in use so as to grip the door handle and provide a tight frictional fit. That is, in the absence of the gripping material, the door handle may be only loosely fit within the cavity, and the gripping material may thus be provided in the form of an insert that fits around the door handle in the cavity to provide a tighter fit and to prevent relative movement between the body of the device and the door handle. The gripping material may thus prevent (or reduce) lateral movement between the body of the device and the door handle. The gripping material may additionally prevent (or reduce) relative twisting or sliding movement between the body and the door handle.

The gripping material may comprise any suitable material or materials having a desired compressibility or providing a desired gripping function. For instance, the gripping material may comprise a resilient material such as silicone. The gripping material may comprise a foam, or a rubber material.

The one or more pieces of gripping material may be provided on the (interior) surface(s) of the parts defining the cavity. Gripping material may additionally be provided at various other suitable locations to prevent or reduce relative movement between the body and a door handle received within the cavity.

The self-cleaning material may comprise an antimicrobial agent such as silver. It will be appreciated that the self-cleaning material may be provided in various ways, so long as the surface(s) of the device have the desired self-cleaning properties. However, in some preferred embodiments, the self-cleaning material may be provided as a coating (layer) on an external surface of the device, e.g. for reasons of manufacturing ease and cost. The device may suitably be coated by spraying, or painting, the self-cleaning material onto the external surface of the device. However, it will be appreciated that any other suitable coating techniques may be used to coat the device with self-cleaning material, e.g. including dip coating or vapour deposition.

The device may be arranged to dispense a fragrance. For instance, especially where the device is installed on a toilet door handle, it may be desired for the device to additionally act as an air freshener so as to mask unpleasant odours. By arranging the device to dispense a suitable fragrance, this may help enhance the user's perception of cleanliness.

From another aspect there is provided a method of installing a device substantially as described herein onto a door handle, the method comprising bringing the plurality of parts into mutual locking engagement around the door handle such that at least a portion of the door handle is substantially enclosed within the cavity.

For instance, where the device is formed of first and second parts, the method may involve bringing the second part of the device into contact with the door handle, and then bringing the first part of the device into mutual locking engagement with the second part around the door handle. For example, where the first and second parts are configured to define a pivot point as described above, the first part may be pivoted into mutual locking engagement with the second part.

The method may comprise bringing the plurality of parts (or e.g. the first and second parts) into mutual locking engagement via a press fit. The mutual locking engagement may be provided by a press fit alone, such that there are no screws or adhesive used to lock the parts together. Thus, the device may be installed relatively easily, e.g. by a layperson, and without requiring any tools.

From yet another aspect there is provided a kit of parts comprising a device substantially as described herein in combination with one or more separate pieces of gripping material. The gripping material may comprise gripping material of the type described herein in relation to any of the other aspects or embodiments of the invention.

The kit may further comprise a measuring tool for measuring a size of a door handle, and wherein the kit comprises a plurality of different pieces of gripping material, wherein the different pieces of gripping material are intended for use with different sizes of door handle.

From a further aspect, a method of using the kit may comprise measuring a size of a door handle, selecting from the plurality of different pieces of gripping material the piece(s) of gripping material intended for use with the measured size, and inserting the selected piece(s) of gripping material into the first and/or second parts of the device. The aspects and embodiments described above relate to a first main embodiment of the invention wherein a device is provided for mounting around a door handle such as a pull bar or a lever handle.

However, the problem of cross-contamination also applies to doors having push plates i.e. wherein the door is arranged to be pushed open by a user exerting a force onto a push plate e.g. provided in the form of a substantially rectangular plate mounted on the lock stile of a door.

Thus, from another aspect, in accordance with a second main embodiment of the invention, there is provided a push plate comprising:

a first plate for fixing to a door; and a second plate at least partly coated, impregnated, or otherwise provided with a self-cleaning material, wherein the second plate is configured to releasably attach to the first plate in order to form a composite push plate structure presenting a self-cleaning external surface.

Thus, the composite push plate structure is defined by (at least) a first plate that, in use, is fixed onto a door, and a second plate that is attached to the first plate and thus defines the outwardly facing external surface of the push plate. That is, the outwardly facing surface of the second plate (and hence of the installed push plate) is the surface that is contacted in use by a user's hands when pushing the door open. In other words, the first plate may define the "back plate" of the composite push plate structure whereas the second plate may define the "front plate".

In embodiments, when the second (e.g. front) plate is attached to the first (e.g. back) plate to form the composite push plate structure, the second plate may generally cover the first plate such that the external surface of the composite push plate structure is provided by the second plate, and, preferably, such that the external surface of the composite push plate structure is substantially flat and/or smooth. For instance, the second plate may cover any fixings or connections used to fix the first plate to the door and/or to attach the second plate to the first plate. By providing a substantially flat and/or smooth external surface, e.g. a surface having no protruding screws or other fixings, the push plate is better able to prevent germs harbouring on the external surface as there are no 'dirt traps' on the surface.

Thus, the first and second plates are typically of substantially the same size and shape as each other. However, it is also contemplated that the first and second plates may be of different sizes and/or shapes. For example, the second plate having the self-cleaning material provided thereon may cover only a portion of the first plate. Alternatively, the second plate may be larger than the first plate.

The second plate may be directly attached to the first plate to form the composite push plate structure. However, it is also contemplated that the composite push plate structure may comprise various other components e.g. intermediate plate structures such that the first and second plates may only be indirectly attached to one another. Regardless, the first plate is generally intended for (semi-)permanent fixing to the door. For example, the first plate may be screwed onto the door and may thus comprise a plurality of suitably arranged holes for receiving screws for fixing the back plate to the door. By contrast, the second plate is intended to be releasably attached to the first plate, so that the second plate may readily be removed and replaced in use e.g. so that the second plate may be replaced as the self-cleaning material wears off or loses efficacy.

The first and second plates may be provided with various connection means for providing a suitable releasable attachment. Preferably, the second plate may be released from attachment with the first plate by a user without using any tools. Thus, the first and second plates may be mechanically connected using various clips in a similar manner as described above in relation to the first main embodiment.

However, in embodiments, the second plate may be configured to magnetically attach to the first plate in order to form the composite push plate structure. Thus, one or more or a plurality of magnets may be provided on either of the first plate or the second plate with one or more corresponding metallic portions or strips provided on the other of the second plate or first plate in order to provide the magnetic attachment. The magnetic attachment serves to hold the composite push plate structure together in normal use, whilst allowing the second plate to be easily removed from the first plate without requiring any special tools e.g. by a user pulling on the second plate.

Typically, because the first plate is intended to be (semi-)permanently fixed to the door whereas the second plate is intended to be replaceable as the self-cleaning material wears off, it may be preferred for the first plate to comprise one or more magnets and the second plate to comprise one or more metallic portions or strips for magnetically attaching to the one or more magnets of the first plate. However, it is also contemplated that one or more magnets may be provided on the second plate, with corresponding metallic portions provided on the first plate, or that each of the first and second plates may comprise a combination of magnets and metallic portions. The magnets and metallic portions may generally be recessed into the first and/or second plates so that they are flush with the surface of the first and/or second plates.

Of course, either of the first and/or second plates may themselves be formed from magnetic material to allow the magnetic attachment. However, it has been found, for reasons of cost and practicality, that it may generally be desirable to form the first and second plates from non-magnetic materials. For example, the second plate may typically be formed from a plastic material, particularly a hard plastic material such as ABS plastic, as these materials may be well suited for receiving the self-cleaning material, and for providing a relatively cheap and robust replaceable front plate. The first plate may typically be formed from aluminium, or other such materials having an appropriate strength and (light) weight for fixing onto a door. In general, the first and second plates may both be formed from rigid or hard materials e.g. a material that does not deform in use when contacted by a user (such as a foam or sponge).

To further facilitate the attachment between the first and second plates, the first plate and/or the second plate may comprise one or more alignment features for aligning the plates together. For example, the alignment features may comprise one or more protrusions provided on one of the first plate and the second plate and one or more corresponding recesses for receiving the protrusions provided on the other of the first plate and the second plate. Thus, (only) when the second plate is brought into correct alignment with the first plate, the second plate may then be pushed into attachment with the first plate. For example, in one embodiment, the first plate may be provided with one or more, such as two, three, four or more, protrusions (or "studs") protruding from the front surface of the first plate (i.e. the surface that faces outwardly when the first plate is fixed to a door). The second plate may thus be provided with a corresponding number of recesses (or "pins") for aligning with these protrusions.

Similarly to the first main embodiment described above, a push plate according the second main embodiment may further comprise an indicator for providing a visual indication of a condition of the device such as a condition that the device should be replaced or renewed and/or a visual indication of an elapsed time period. Thus, as the self-cleaning material provided on the second plate wears off during use, a visual indication of this, or of the life of the push plate device, may be provided to users to indicate when the front plate should be replaced. The indicator is typically provided on the second plate so as to indicate that the second plate needs to be replaced. As described above, the indicator may indicate an elapsed time after activation of the indicator. For example, the indicator may comprise a colourant, wherein the colourant is released upon activation of the indicator and caused to wick a substrate, wherein the amount of wicking indicates an elapsed time period. The indicator may be activated manually by a user prior to the user attaching a second plate onto a fixed first plate. However, in embodiments, the indicator may be activated automatically as the second plate is attached to the first plate. For instance, the indicator may be mounted on the second plate, and a suitable protrusion may be provided on the first plate so that when the first and second plates are brought into correct alignment and attachment, the protrusion activates the indicator.

The second plate may comprise a window such that the indicator is viewable from the external surface of the composite push plate structure through the window.

Various suitable self-cleaning materials may be used, as explained above in relation to the first main embodiment. Generally, any features of the self-cleaning material described above apply equally to the self-cleaning material that may be used in accordance with the second main embodiment. Thus, in embodiments, the self-cleaning material may comprise an antimicrobial agent such as silver. As explained above, the self-cleaning material may be provided on the second plate in any suitable and desired manner. However, in some preferred embodiments, the device is coated with self-cleaning material, e.g. by a spraying, or other suitable coating, process.

From another aspect there is provided a method of using a push plate substantially as described above in relation to the second main embodiment of the invention, the method comprising:

fixing the first plate onto a door; and
attaching a second plate to the first plate to define a composite push plate structure.

The method may further comprise removing the second plate from the first plate, and attaching a different second plate to the first plate. That is, the first plate may be fixed onto the door, and used with a plurality of different second plates, with the second plates being replaced e.g. when the self-cleaning material has worn off, or after a pre-determined period of time. Where the push plate comprises an indicator device, the method may further comprise a step of activating the indicator device. The step of activating the indicator device may be performed prior to the step of attaching a second plate to the first plate, or may happen automatically as a second plate is attached to the first plate.

BRIEF DESCRIPTION OF THE DRAWINGS

Various embodiments will now be described, by way of example only, and with reference to the accompanying drawings in which.

DETAILED DESCRIPTION

Figure 1:
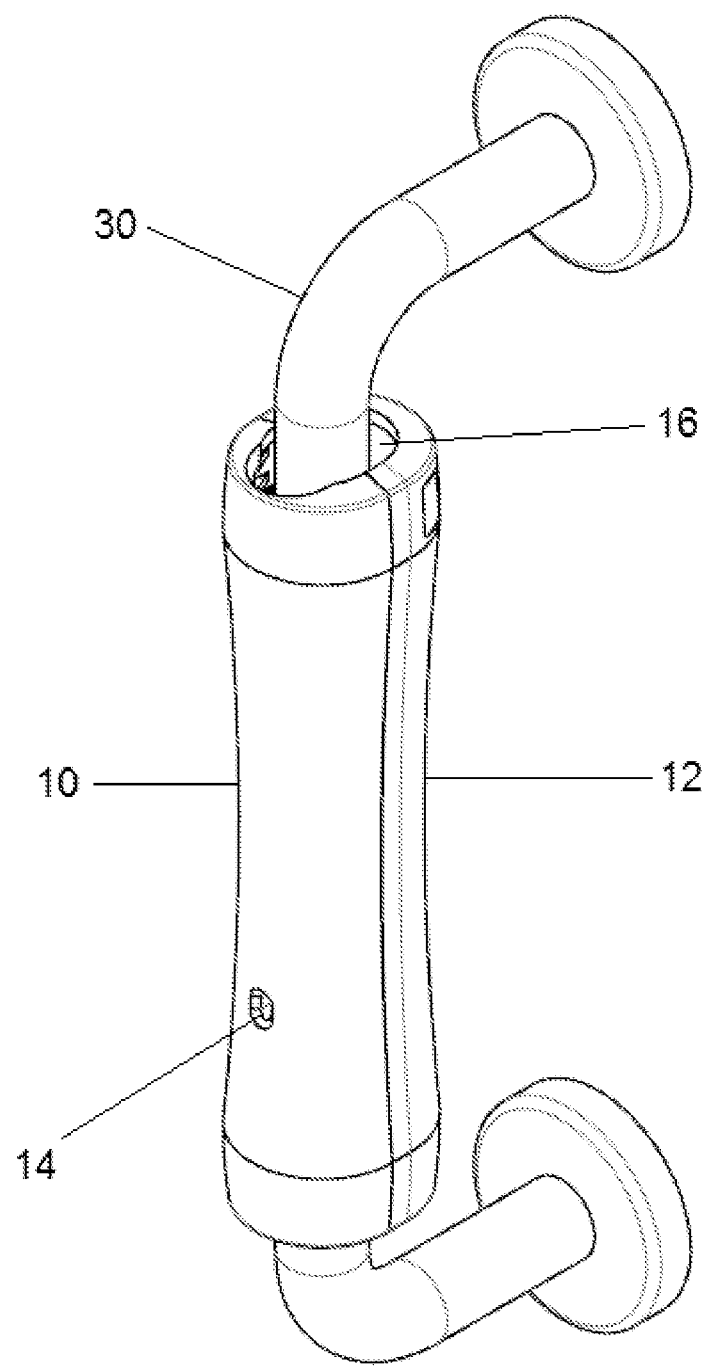
FIG. 1 shows a device according to a first main embodiment of the invention mounted around a door handle.

FIG. 1 shows an example of a device according to a first main embodiment of the invention mounted around a door handle 30. The body of the device is formed from separate first 10 and second 12 parts, which are arranged for mutual locking engagement with one another. When the first 10 and second 12 parts are mutually engaged, as shown in FIG. 1, a cavity 16 is defined between the first and second parts that is suitably dimensioned for receiving a door handle. Thus, in use, the first and second parts may be brought together into mutual locking engagement around the door handle in order to mount the device to the door handle 30 in the manner illustrated.

Figure 2:
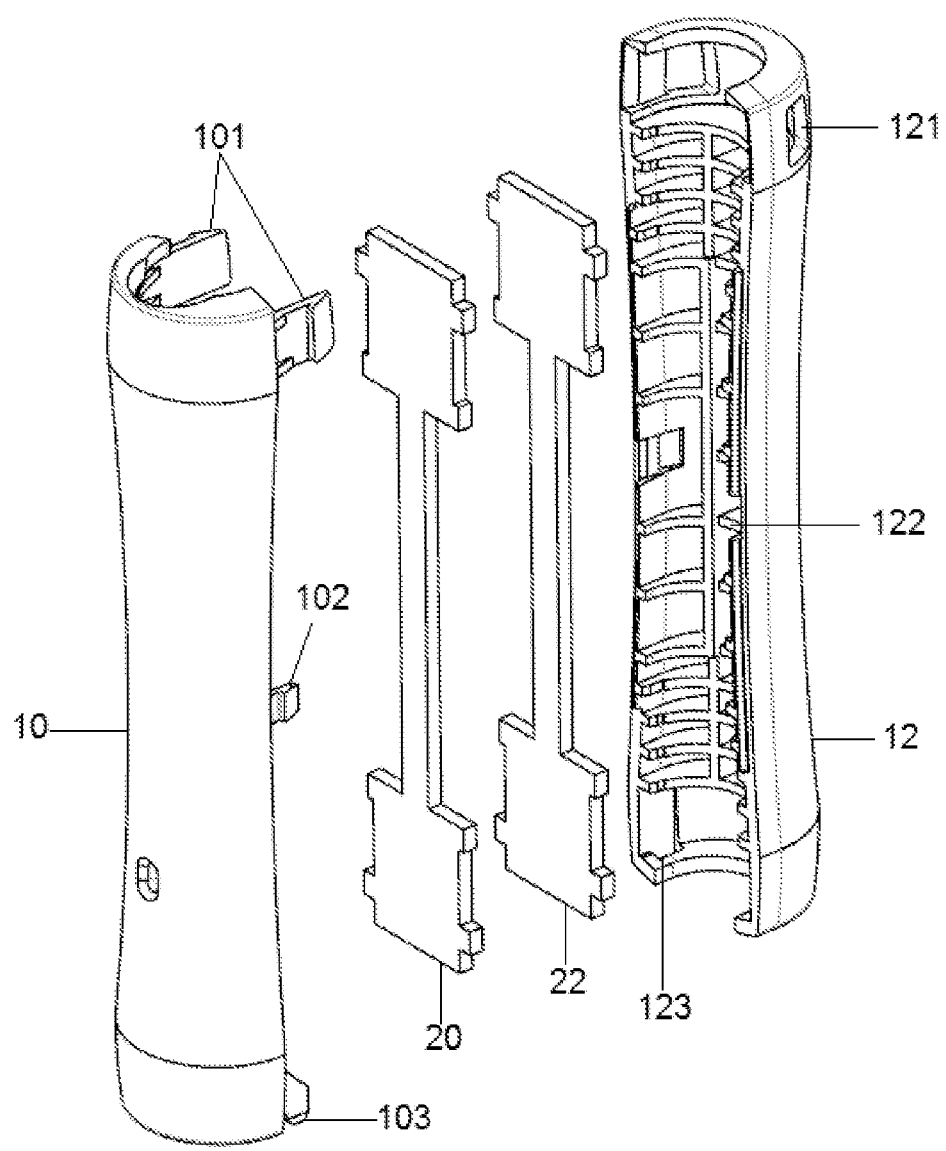
FIG. 2 shows an exploded view of the device of FIG. 1.

FIG. 2 shows an exploded view of the components of the device of FIG. 1. In particular, FIG. 2 shows the separate first 10 and second 12 parts that may be brought into mutual engagement with one another. To provide the mutual locking engagement, the first part 10 and/or the second part 12 may comprise various tabs or protrusions that engage with corresponding portions of the other part in order to provide the mutual locking engagement. For example, as illustrated in FIG. 2, a first tab 103 may be provided at the base of the first part 10 with a corresponding recess 123 provided at the base of the second part 12. The first tab 103 may be received within the corresponding recess 123 to provide a pivot point such that, after the first tab 103 is inserted into the corresponding recess 123, the remainder of the first and second parts may be pivotally brought into engagement with one another. To lock the first and second parts together, a second tab 101 may be provided near the top of the first part 10 with a corresponding recess 121 at the top of the second part 12. As the first and second parts are pivoted towards each other, the second tab 101 may be press fit into its corresponding recess 121 in order to lock the first and second parts together. The second tab 101 may be releasably clipped into its corresponding recess 121 to allow the first and second parts to be subsequently disengaged by a user, e.g. when it is desired to remove or replace the device. A third tab 102, or further tabs, may also be provided, with corresponding recess(es) 122, to further facilitate the engagement of the first and second parts.

Figure 3:
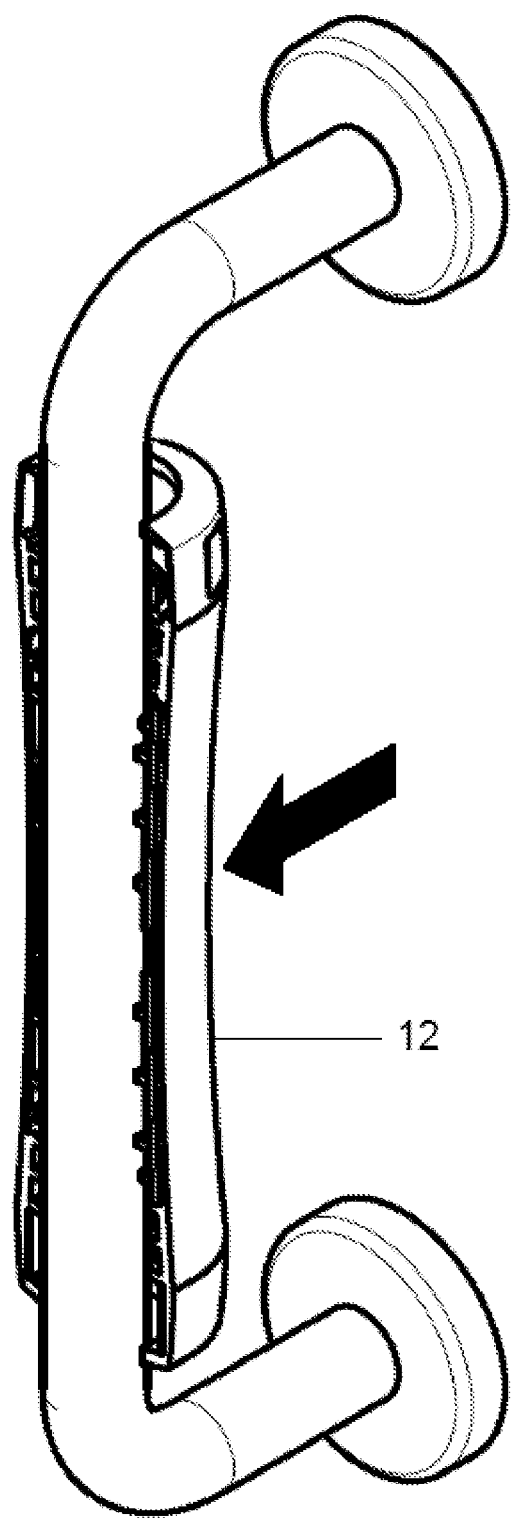
FIG. 3 illustrates a first step of the process for mounting the device around a door handle.
Figure 4:
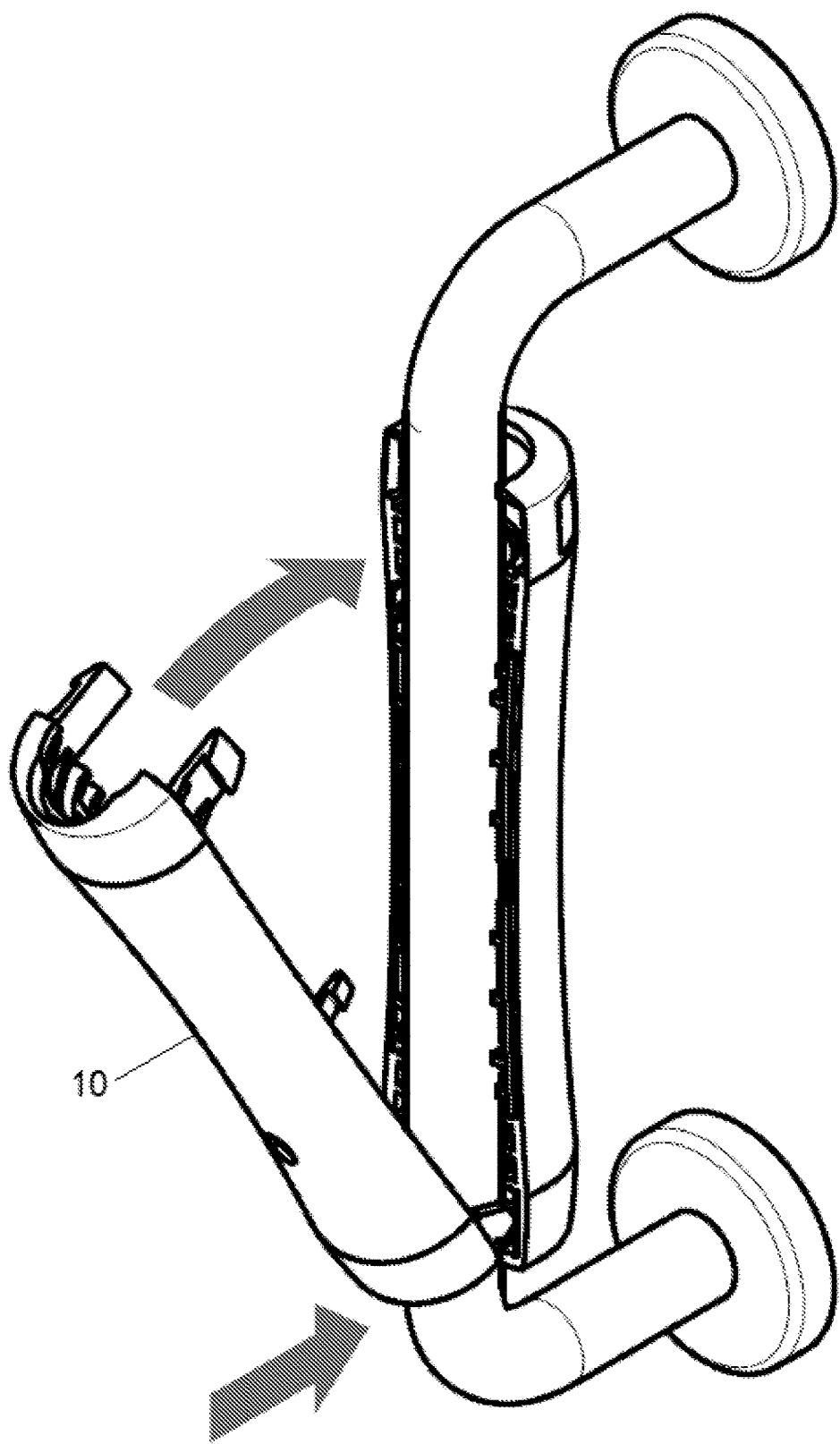
FIG. 4 illustrates a second step of the process for mounting the device around the door handle.

The process of mounting the device to a door handle is illustrated in FIGS. 3 and 4. In a first step, shown in FIG. 3, the second part 12 of the device (forming the rear part) may be held against the rear of the door handle. The first part 10 may then be aligned with the second part 12, in particular by engaging the lowermost tab 103 of the first part 10 with the corresponding recess 123 of the second part 12, and then brought into engagement with the second part 12 by pivoting the first part 10 towards the second part 12, as shown in FIG. 4, and then pushing the parts together such that the other tabs 101,102 clip into place. In this way, the device may be securely mounted around the door handle, i.e. as shown in FIG. 1. It will be appreciated that this mounting process is relatively simple, and does not, for instance, require any special tools or skills. The device described herein may therefore be suitable for installation by a layperson.

It will be appreciated that the manner of locking engagement described above in relation to FIGS. 1 to 4 is merely exemplary, and that various other suitable arrangements for having the first and second parts releasably engage with one another may equally be used with any or all of the other features described herein. Such other arrangements will be readily apparent to a person skilled in the art.

With the device mounted around the door handle as shown in FIG. 1, a user is forced to grip the device in order to use the door. The device therefore essentially acts as a cover for the door handle. Any germs present on the user's hands are therefore transferred to the device rather than the door handle itself. By coating the first part 10 and/or the second part 12 (or at least the portions thereof touched by a user) with a self-cleaning material such as an antimicrobial agent, any germs transferred to the surface of the device will be killed, thus helping to prevent the spread of germs from one user to another. The device is therefore self-cleaning.

The first and second parts may suitably be formed from a hard plastic material, such as ABS plastic, coated with the antimicrobial agent. However, it will be appreciated that the first and second parts may equally be formed from various other suitable materials, that may be selected e.g. on the basis of their durability and/or ease of manufacture.

Various self-cleaning materials are known that may be suitably used for coating the device and/or being impregnated into the parts. Generally, as well as having the desired antimicrobial or particularly antibacterial properties, the self-cleaning material should be non-toxic, and should be effective for an extended period of time, to avoid having to replace the device too often. Antimicrobial agents such as silver have been found to be particularly suitable in this context. For instance, the self-cleaning material may comprise ionic silver particles. The silver particles may e.g. be provided as an additive within a conventional paint coating, with the coating being applied to the first and/or second parts via spray painting. Naturally, the coating may also include other additives, including additives that do not provide an antimicrobial effect but are provided for other reasons.

The silver ions embedded in the coating layer may then be released, in use, via ambient moisture, or moisture from a user's hand, such that the silver ions can enter the cell membranes of any germs present on the surface of the coating layer. The silver ions destabilise the cell, stop respiration and inhibit cell division, whilst blocking the replication of DNA. The use of silver as an antimicrobial agent in general is well known.

In general, the antimicrobial agent may be provided on the surface of the first and/or second parts in any suitable way, and need not be provided as a coating. For instance, and depending on the material used to form the first and second parts, the antimicrobial agent may be impregnated within the first and second parts. Alternatively, or additionally, the antimicrobial agent may be arranged to be dispensed through the first and second parts, e.g. where the first and second parts are porous or are provided with apertures for dispensing the antimicrobial agent. Alternatively still, the first and/or second parts may be formed, at least in part, from a material having self-cleaning properties.

Over time, the self-cleaning material will eventually wear off, or otherwise become lost, with use of the device. The device may also become scratched with repeated use. As shown in FIG. 1, an indicator 14 may thus be provided to indicate to a user when the device should be renewed or replaced. Generally, the indicator 14 may be provided anywhere on the device so long as it is suitably visible in use. For example, in FIG. 1 the indicator 14 is provided on the front portion of the device for maximum visibility.

The indicator 14 may comprise a window formed in the first (front) part 10 of the device, as shown in FIG. 1, with an indicator device mounted behind the window on the interior of the first part 10 such that the indicator device, or at least a portion thereof, is visible through the window from the exterior of the device. Various suitable indicator devices may be used for this purpose. One particularly suitable form of indicator device may comprise a colourant that is caused to 'wick' a substrate, with the amount of wicking indicating an elapsed time after activation of the indicator device. For example, the colourant may initially be sealed within a reservoir, and the indicator device activated by breaking the seal to release the colourant and allow the colourant to start wicking. The step of activating the indicator device thus defines the start of the indicator measurement. The indicator device may then progressively indicate how long has elapsed since the indicator has been activated, so that a user can determine whether the device may need to be replaced. Alternatively, the indicator may simply indicate the expiry of a pre-determined time interval. For instance, a user may be instructed to replace the devices after a set period, e.g. of six months. The indicator 14 may thus be arranged to indicate when a period of six months has elapsed, e.g. by changing colour, e.g. by having the colourant pass behind the window so that it is visible through the window from the exterior of the device.

In embodiments, the indicator 14 is arranged such that the indicator is activated upon bringing the first and second parts into mutual engagement. For example, for the indicator described above, the locking engagement of the first and second parts may break the seal and start the wicking process.

Various other forms of indicator may also be used, and the indicator may also be mounted in various suitable ways. For instance, the indicator may alternatively be mounted externally on the device such that no window needs to be provided to view the indicator.

It will be appreciated that there is no standard shape for a door handle. The device shown in FIGS. 1 and 2 is arranged to fit around a substantially cylindrical "pull" door handle, however, even for this type of door handle there is no standard diameter. To allow the device to be retrofitted onto a range of different diameter door handles, the cavity 16 is oversized (relative to typical door handle diameters) and a gripping material 20,22 may be provided on the respective surfaces of the first and second parts defining the cavity 16. The gripping material 20,22 may comprise any suitable resilient padding material capable of compressing between the first and second parts and the door handle to provide a tight (or at least tighter) fit around the door handle. For example, the gripping material may comprise a foam, rubber or silicone material.

Generally, the gripping material 20,22 may be provided as one or more insert(s) that are pressed into the first and/or second part(s). This is shown in FIG. 2, for example. The gripping material may be adhesively attached to the interior surfaces of the first and/or second parts, or may be held in place by frictional forces.

Figure 5:
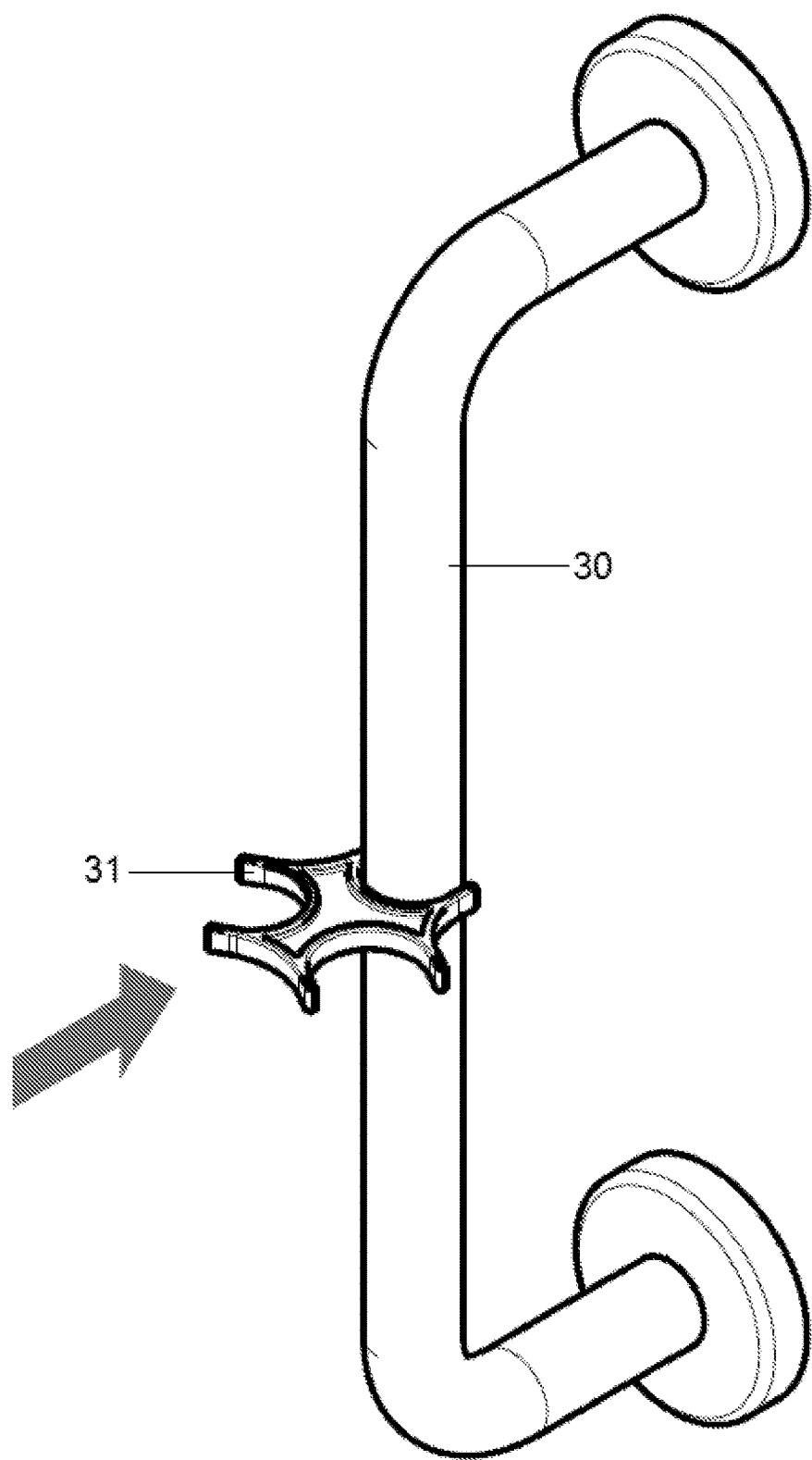
FIG. 5 shows a measuring tool for measuring a diameter of a device.
Figure 6:
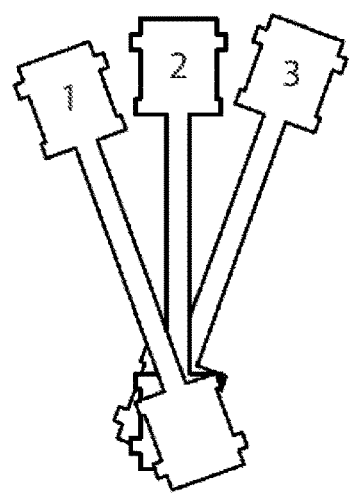
FIG. 6 shows a set of pieces of gripping material.
Figure 7:
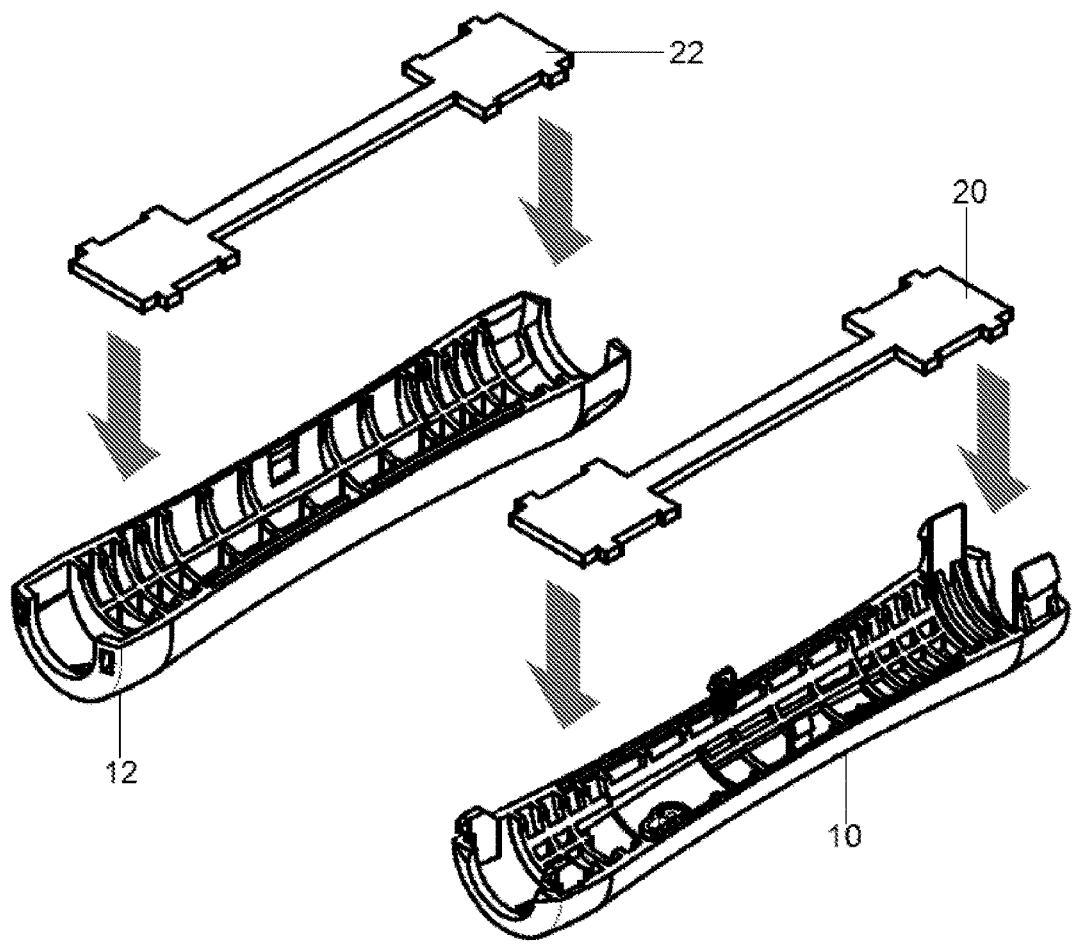
FIG. 7 shows the gripping material being inserted into position within the device.

It is contemplated that the device may be sold as part of a kit with a plurality of different sized or shaped pieces of gripping material suitable for different diameter door handles. As shown in FIG. 5, a measuring tool 31 may also be provided with the kit for measuring a dimension of a door handle 30 to which the device is to be fitted. Based on this measurement, the user can then select the most suitable shape or size piece(s) of gripping material from those provided within the kit (see FIG. 6). Once the most appropriate shape or size piece(s) of gripping material 20,22 have been selected, these are then pressed into position within the first and second parts as shown in FIG. 7.

The gripping material 20,22 may also act to prevent relative movement between the device and the door handle in use, such as twisting or sliding movement that may be disconcerting to a user. Thus, the gripping material helps to provide a secure, tight fit, across a range of door handle diameters. To facilitate this, the gripping material may optionally be provided with a degree of tackiness or adhesiveness to facilitate securing the device to the door handle, so long as this does not prevent the device being readily replaceable by a user (i.e. if adhesive is used, it should be relatively weak). In embodiments, additional strips of adhesive material may be provided to further reduce any relative movement between the device and the door handle. However, the frictional forces between the gripping material 20,22 and the body alone may be sufficient to prevent relative movement, and it is not generally necessary to adhere the door handle to the body.

In some embodiments, the device may be arranged to dispense a fragrance to help mask any unpleasant odours and/or to enhance the user's perception of cleanliness. It will be appreciated that the device may be arranged to dispense a fragrance in any suitable fashion. For example, a recess may be provided in either the first or second part for receiving a vial of fragrance. The vial may be inserted into the recess, and the user may then open the vial as, or shortly after, they fit the first or second part to the door handle. As another example, a fragrance may be impregnated or coated on the first or second part, so long as the fragrance does not detriment the self-cleaning properties of the device. As yet another example, a packet or vial of fragrance provided within the device may be broken when the device is installed on a door handle, in a similar manner to that described above in relation to the activation of the indicator 14, such that fragrance is dispensed only after the device is installed. For instance, the fragrance may be dispensed through the ends of the cavity of the device, or through further ports or apertures provided on the body of the device.

Although the door handle 30 shown in FIG. 1 is a pull door handle in the form of an extended cylindrical bar mounted to the door at either end, it will be appreciated that the invention need not be limited to any specific type of door handle. By varying the relative shapes and/or sizes of the first and second parts, and hence of the cavity 16, it is possible to accommodate a wide variety of shapes and/or sizes of door handle. Thus, whilst the cavity 16 shown in FIG. 1 is substantially cylindrical and extends throughout the body of the device, different cavity shapes may be used to allow the device to be mounted onto different shaped door handles.

Figure 8:
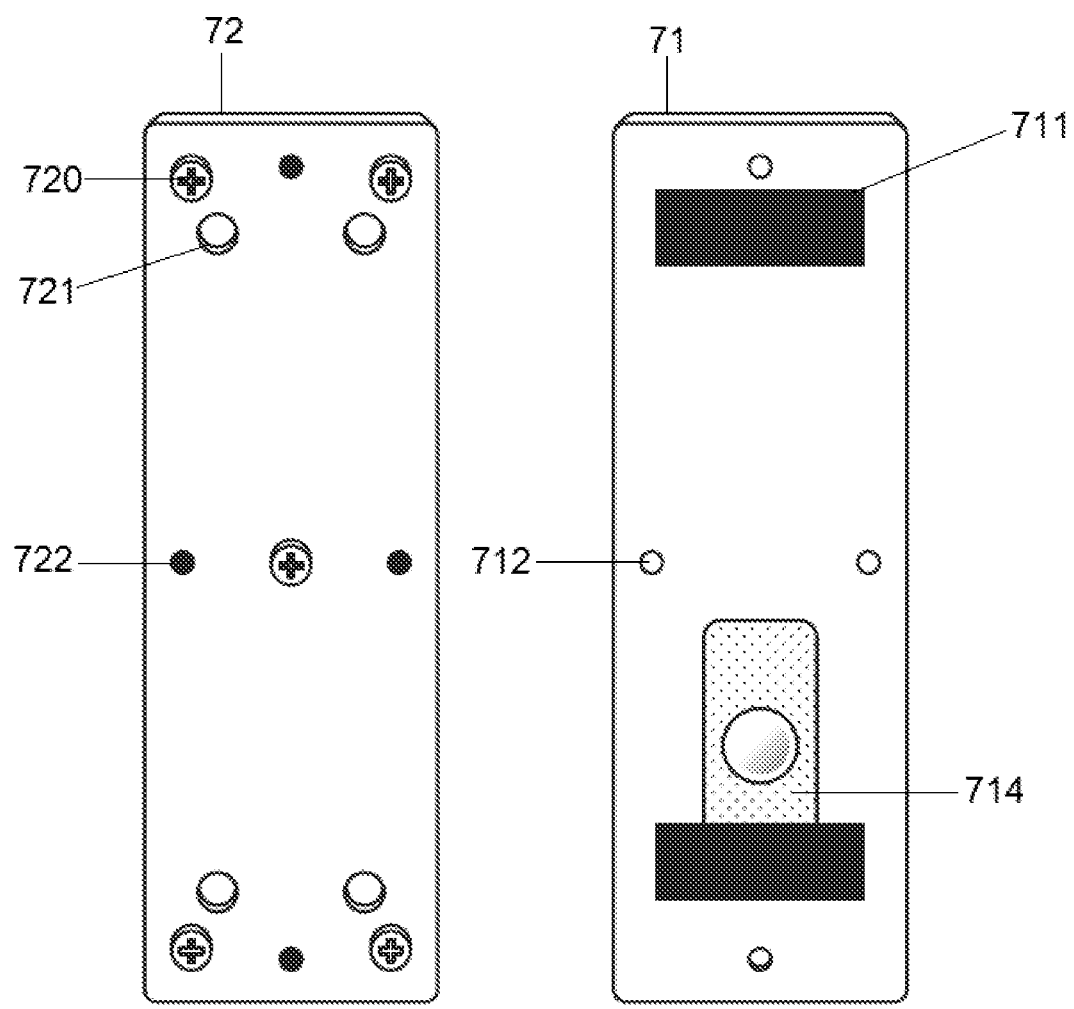
FIG. 8 shows front and back plates for forming a composite push plate according to a second main embodiment of the invention.
Figure 9:
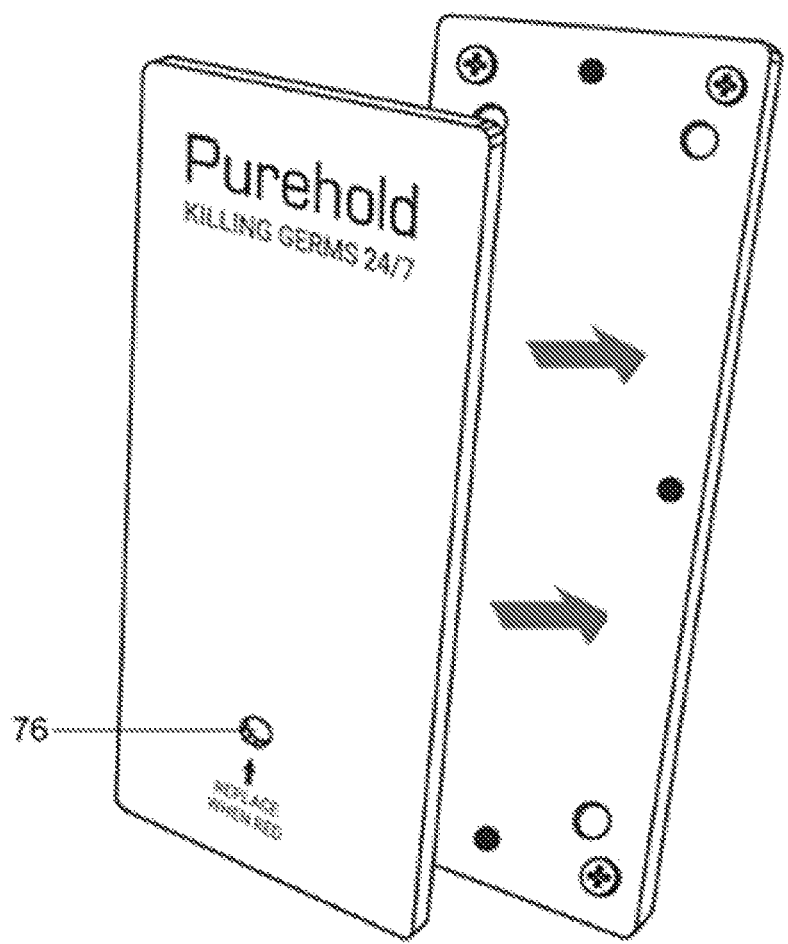
FIG. 9 shows how the front and back plates of FIG. 8 may be attached together to form a composite push plate structure.
Figure 10:
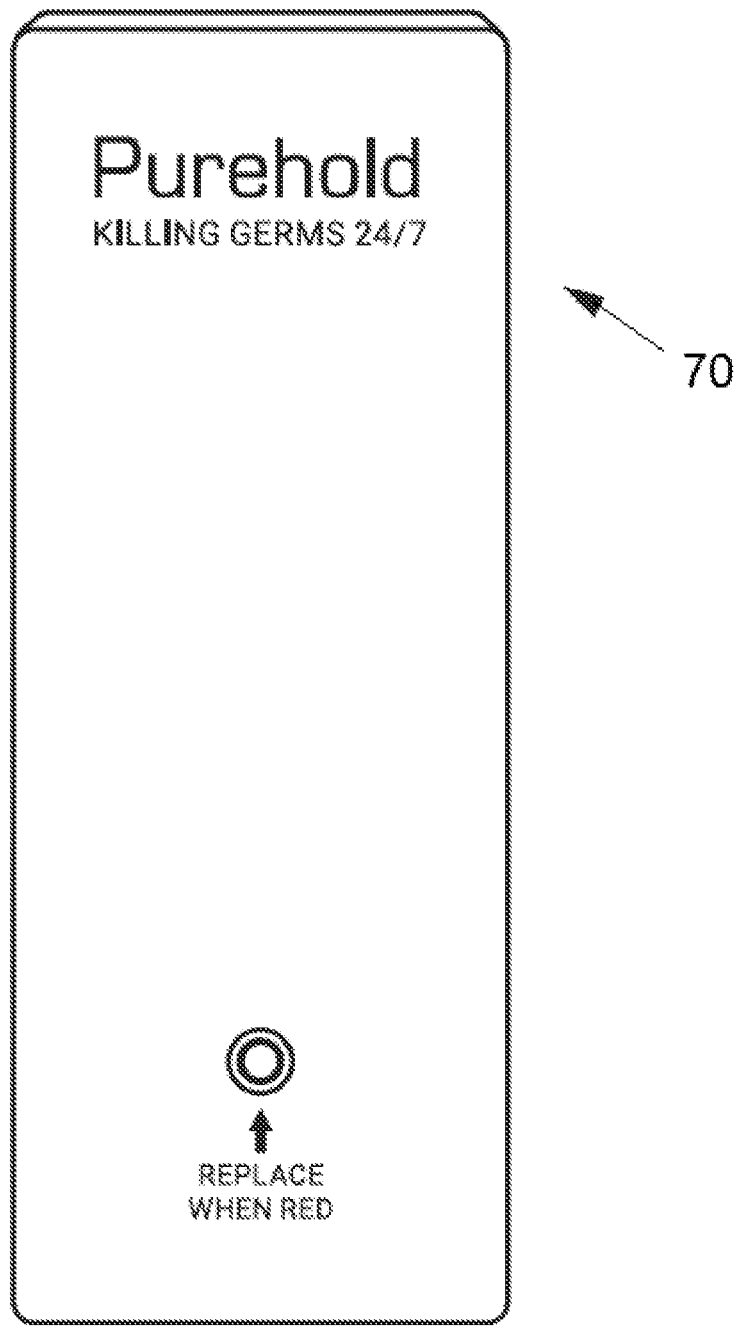
FIG. 10 shows the completed push plate.

FIG. 8 illustrates a front plate 71 and a back plate 72 that may be attached together as shown in FIG. 9 to form a composite push plate structure for a door. The final push plate 70 as may be fixed onto a door is shown in FIG. 10. The push plate 70 is thus a composite plate structure comprising the front plate 71 mounted onto the back plate 72. The front plate 71 may be coated with a self-cleaning material, e.g. of any of the types described above in relation to the first main embodiment of the invention, so that the external surface of the push plate 70 that is contacted by a user's hands when the push plate 70 is installed on a door is self-cleaning. Furthermore, as best shown in FIG. 10, the external or outwardly facing surface of the push plate 70 may be essentially flat and smooth (save for an indicator window 76, where one is provided), in contrast to conventional push plates wherein the screws for fixing the push plate to the door protrude slightly and potentially form dirt traps where germs may accumulate.

In a first step of installing the push plate 70 into a door the back plate 72 may be fixed onto the door stile. The back plate 72 may e.g. comprise a fixing adhesive or tape on its rear side so that the back plate 72. However, preferably, the back plate 72 comprises a plurality of screw holes 720, as shown in FIG. 8, so that the back plate 72 may be screwed onto the door to provide a semi-permanent fixing. That is, once the back plate 72 is fixed (e.g. screwed) onto the door, it may not be readily removed other than by unscrewing it.

Once the back plate 72 is fixed (e.g. screwed) onto the door, a front plate 71 may then be brought into alignment and attachment with the back plate 72 in order to define a composite push plate 70 (FIGS. 9 and 10). By contrast to the back plate 72, which is intended to be semi-permanently fixed to the door, the front plate 71 is intended to be releasably connected to the back plate 72 such that the front plate 71 may be readily removed and replaced by a user without requiring any tools. For example, the front and back plates may be releasably connected with one another using a magnetic connection. It will be appreciated that the materials typically used to form the front plate 71 and the back plate 72 may be non-magnetic. For example, the front plate 71 may typically be formed from a hard plastic material, such as ABS plastic, similarly to the materials that are suitably used to form the parts in accordance with the first main embodiment. The back plate 72 may typically be formed of aluminium. Thus, a plurality of magnets 721 may be provided on the back plate 72 that are suitably positioned so as to magnetically connect with suitable metallic portions (e.g. strips) 711 provided on the interior of the front plate 71 in order to hold the composite push plate 70 together. The front plate 71 and back plate 72 may be suitably recessed or may comprise suitable receptacles for receiving the appropriate magnets 721 and/or metallic portions 711 so that the magnets and metallic portions are provided flush with the internal surfaces of the plates (i.e. those illustrated in FIG. 8).

In general, it will be appreciated that the releasable connection between the plates need not be magnetic, and that various other suitably releasable connections may be used. For example, the connection may be a mechanical connection, similar to the connections used in the first main aspect of the invention.

However the connection is formed, the connection should be releasable so as to allow a user to readily remove the front plate 71 from the back plate 72 without requiring any specialist tools, to facilitate users replacing the front plate 71 when the self-cleaning surface is worn out.

To further facilitate the attachment of the front plate 71 to the back plate 72, either or both of the plates may be provided with suitable guiding or alignment features. For example, the back plate 72 may comprise a plurality of studs 722 protruding from its front surface that act as anchors for corresponding recesses 712 providing on the internal surface of the front plate 71. The studs may thus align with and attach to the recesses in order to help prevent any movement of the front plate 71 during normal use of the push plate 70.

The front plate 71 may further be provided with an indicator 714, which may be of substantially the same type as the indicator 14 described above in relation to the first main embodiment of the invention. Accordingly, as shown in FIG. 9, a time indicator window 76 may be provided on the front plate 71 for viewing the indicator 714 so that the user is provided with an indication of when it is time to replace the front plate 71 e.g. due to wearing of the self-cleaning surface over time due to scratching. As shown in FIG. 8, the indicator 714 may be mounted on the internal surface of the front plate 71 and is aligned with the indicator window 76 so that at least the indicator portion is visible through the indicator window 76. Prior to fitting the front plate 71 onto the back plate 72, the indicator may be activated by a user depressing the indicator. However, it is also contemplated that the indicator may be activated by the action of fitting the front plate 71 onto the back plate 72. For example, where the time indicator 714 is mounted onto the front plate 71, a corresponding protrusion (not shown) may be provided on the back plate 72 so that when the front plate 71 is pushed onto the back plate 72, the protrusion presses against and activates the indicator 714. Although the indicator as shown in FIG. 8 may typically be provided on the front plate 71, so that the indicator is associated with and replaceable at the same time as the front plate 71, it will be appreciated that the indicator might also suitably be provided on the back plate 72, or on a further or intermediate component of the composite push plate 70.

FIG. 10 shows the composite push plate 70 in the form as it may be mounted onto a door. As shown in FIG. 10, the indicator 714 is visible from the exterior of the push plate 70 through the indicator window 76 provided on the front plate 71. As explained above, when the indicator changes colour, the user is prompted to remove and replace the front plate 71.

Although the present invention has been described with reference to various embodiments, it will be understood by those skilled in the art that various changes in form and detail may be made without departing from the scope of the invention as set forth in the accompanying claims.

The invention claimed is:

1. A device for mounting to a pull bar type door handle comprising:
a plurality of parts,
the parts being configured for mutual locking engagement such that when the plurality of parts are brought into mutual locking engagement around a door handle at least a portion of the pull bar door handle is substantially enclosed within a cavity formed between the plurality of parts, the cavity being defined by respective interior surfaces of the plurality of parts, wherein each of the parts has a curved interior surface such that when the plurality of parts when brought into mutual locking engagement the respective curved interior surfaces of the parts together define the cavity as substantially cylindrical;
wherein at least a portion of at least one of the plurality of parts is coated, impregnated, or otherwise provided with a self-cleaning and/or antimicrobial material,
the device further comprising one or more pieces of resilient gripping material for preventing or reducing relative movement between said device and a door handle received within said cavity, the one or more pieces of resilient gripping material being provided on respective interior surfaces of the parts that are brought into mutual locking engagement to define the cavity for receiving the pull bar door handle.

2. The device of claim 1, comprising a first part and a second part, wherein the first and second parts are configured for mutual locking engagement such that when the first and second parts are brought into mutual locking engagement said cavity is formed between the first and second parts.

3. The device of claim 1, wherein the parts are configured for releasable mutual engagement.

4. The device of claim 1, wherein said parts are configured for mutual locking engagement via a press fit.

5. The device of claim 1, further comprising an indicator for providing a visual indication of a condition of the device and/or a visual indication of an elapsed time period.

6. The device of claim 5, wherein the indicator indicates an elapsed time after activation of the indicator, wherein the indicator is activated when the parts, or at least some of the parts, are brought into mutual locking engagement around a door handle.

7. The device of claim 6, wherein the indicator comprises a colorant, wherein the colorant is released upon activation of the indicator and caused to wick a substrate, wherein the amount of wicking indicates an elapsed time period.

8. The device of claim 5, wherein the condition of the device is that the device should be replaced or renewed.

9. The device of claim 1, wherein said device is arranged to dispense a fragrance.

10. The device of claim 1, wherein the parts are formed from a rigid or hard material.

11. The device of claim 1, wherein the one or more pieces of resilient gripping material comprise one or more inserts which are separately provided on one or more of the plurality of parts.

12. The device of claim 1, wherein the self-cleaning and/or antimicrobial material comprises silver.

13. A device for mounting to a door handle comprising:
a plurality of parts,
the parts being configured for mutual locking engagement such that when the plurality of parts are brought into mutual locking engagement around a door handle at least a portion of the door handle is substantially enclosed within a cavity formed between the plurality of parts,
wherein at least a portion of at least one of the plurality of parts is coated, impregnated, or otherwise provided with a self-cleaning and/or antimicrobial material; and
an indicator for providing a visual indication of a condition of the device and/or a visual indication of an elapsed time period, wherein the indicator indicates an elapsed time after activation of the indicator, wherein the indicator is activated when the parts, or at least some of the parts, are brought into mutual locking engagement around a door handle, wherein the indicator comprises a colorant, wherein the colorant is released upon activation of the indicator and caused to wick a substrate, wherein the amount of wicking indicates an elapsed time period, wherein the colorant is released from a sealed reservoir, and wherein the indicator is configured to indicate the expiry of a predetermined time interval.

14. A device for mounting to a door handle comprising:
a plurality of parts,
the parts being configured for mutual locking engagement such that when the plurality of parts are brought into mutual locking engagement around a door handle at least a portion of the door handle is substantially enclosed within a cavity formed between the plurality of parts;
wherein at least a portion of at least one of the plurality of parts is coated, impregnated, or otherwise provided with a self-cleaning and/or antimicrobial material,
wherein said plurality of parts provide an exterior facing surface that may be contacted in use, and wherein a majority of an exterior facing surface of each part comprises a contact surface which is substantially smooth without any perforations or screw holes, except for a window for viewing an indicator provided on one of the plurality of parts and except for perforations engaged by locking tabs.

15. A kit of parts comprising a device as claimed in claim 1 in combination with a plurality of different pieces of gripping material, wherein the different pieces of gripping material are intended for use with different sizes of door handle.

* * * * *